United States Patent [19]
deMey, II et al.

[11] 4,192,614
[45] Mar. 11, 1980

[54] L/C DETECTOR CELL ASSEMBLY

[75] Inventors: Charles F. deMey, II, West Redding; Charles C. Helms, Trumbull, both of Conn.

[73] Assignee: The Perkin-Elmer Corporation, Norwalk, Conn.

[21] Appl. No.: 928,928

[22] Filed: Jul. 28, 1978

Related U.S. Application Data

[63] Continuation of Ser. No. 547,758, Feb. 6, 1975, abandoned.

[51] Int. Cl.$^2$ ............................................. G01N 21/02
[52] U.S. Cl. ..................................... 356/410; 356/326
[58] Field of Search ................... 356/181, 246, 96, 97, 356/410, 326

[56] References Cited

U.S. PATENT DOCUMENTS

| | | | |
|---|---|---|---|
| 3,022,704 | 2/1962 | Cary | 356/324 |
| 3,551,062 | 7/1967 | Brown | 356/246 |
| 3,606,547 | 9/1971 | Iwahashi | 356/97 |
| 3,614,242 | 10/1971 | Hrdina | 356/181 |
| 3,684,386 | 8/1972 | Noll | 356/246 |
| 3,941,487 | 3/1976 | Ehret et al. | 356/181 |
| 4,019,372 | 4/1977 | Parkell et al. | 356/181 |

Primary Examiner—Vincent P. McGraw
Attorney, Agent, or Firm—S. A. Giarratana; F. L. Masselle; E. T. Grimes

[57] ABSTRACT

A spectrophotometer detector cell assembly having improved sensitivity, has a cell defined by a bore through a body and closed at the ends by radiation transparent windows with inlet and outlet passages through the body to the bore, so that radiation passed through the sample fluid flowing through the bore is detected by a photodetector. The body, which is made of a thermally conductive material, is a large thermal mass is relation to the volume of the cell and a tubular inlet conduit, also made of a thermally conductive material, wraps around the body and connects to the inlet passage so that fluid flowing into the bore will tend to reach a stable temperature due to the heat sink effect of the body and conduit thereby stabilizing the refractive index of the fluid in the bore and enhancing the sensitivity of the photodetection. Sensitivity is further enhanced by focussing the radiant energy entering the bore and by concentrating the exiting radiation in a planar area in which the diameter of the bundle of exiting energy rays does not change with changes in the refractive index of fluid in the cell, and by having the latter area substantially coincide with the photodetector surface.

4 Claims, 3 Drawing Figures

U.S. Patent     Mar. 11, 1980     4,192,614
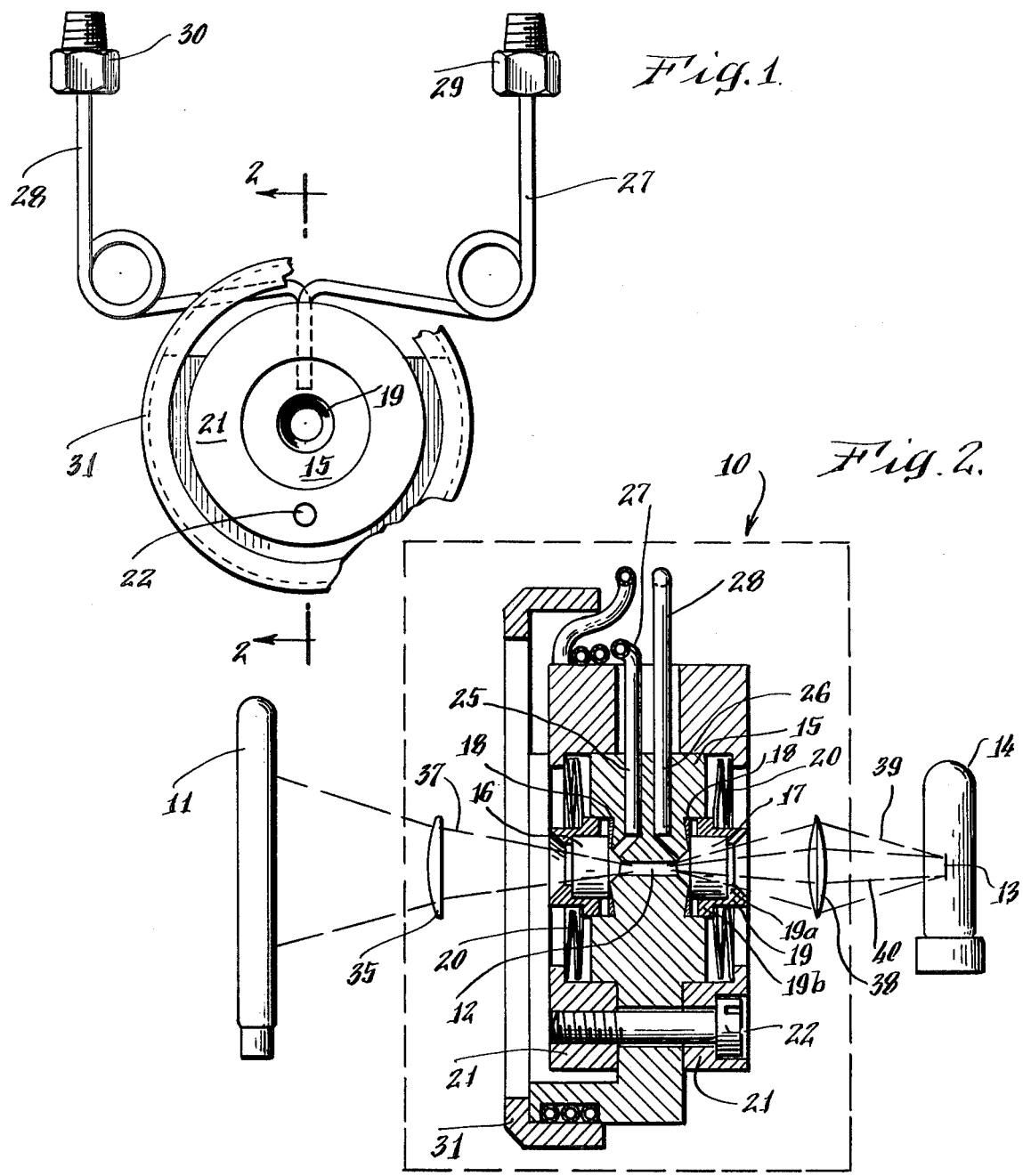
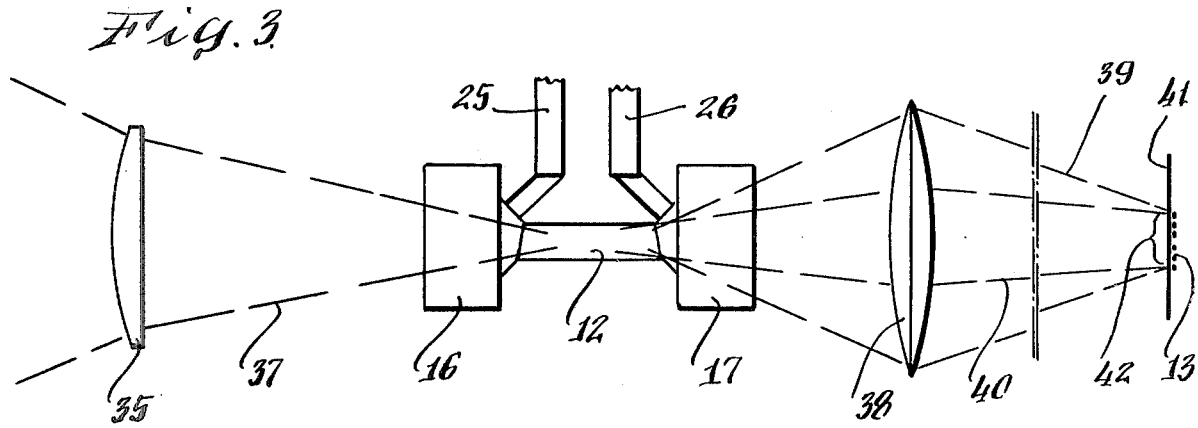

L/C DETECTOR CELL ASSEMBLY

This is a continuation of application Ser. No. 547,758, filed Feb. 6, 1975, and now abandoned.

BACKGROUND OF THE INVENTION

The present invention relates to detectors for spectrophotometers and particularly to a detector for a spectrophotometer of the flow-through type utilizing variable wavelength radiation for liquid chromatography.

In the subject type of spectrophotometers for liquid chromatography a substance whose quantitative presence in a sample is to be determined is dissolved in a suitable carrier solvent and flowed through a detector cell, which has end windows through which ultraviolet or visible light radiation is directed. Radiation exiting from the cell falls on a photodetector whose output is recorded by suitable instrumentation which is calibrated to indicate the amount of radiation absorbed by the fluid flowing through the cell. Absorbance is customarily indicated by a graph continuously recorded on a strip chart by a pen recorder. The quantitative presence of a substance of interest is determined by measuring the area under the graph peaks which represent the amount of radiation of a particular wavelength that is absorbed, particular materials being identified by particular wavelengths characteristically absorbed by them.

The sensitivity of a spectrophotometer detector cell is a function particularly of the stability of the base line of the graph; the graph base line is established by the absorbance of the solvent used, and will change in relation to any change in the refractive index of the solvent, which in turn will be changed by a change in the temperature of the solvent in the cell. When the baseline changes the true peak area can not be measured accurately and the peaks themselves become less clearly defined and hence difficult to identify and measure with any reliable degree of accuracy.

A particular problem affecting sensitivity in conventional spectrophotometers is the inefficient utilization of the radiation applied. In instruments adapted to take measurements with radiation of various wavelengths, the beam characteristics of the source are different for different wavelengths (which may be provided by substituting different radiation sources or by selecting a particular wavelength with a monochromator or with a filter). Therefore, it has been the custom to dimension and mount the detection cell and photodetector in relation to the source so that a minimum diameter source beam of radiation will fill the cell entrance, which means a larger diameter beam will lose some radiation to vignetting at the entrance and, at the other end, the diametric area of exiting radiation impinging on the detector may increase beyond the area of the detector surface, and thus be wasted due to a change in the index of the solvent in the cell. Consequently, much of the radiation applied is lost and only a portion of the exiting beam is recorded. Consequently, the sensitivity of the instrument which is rather limited in the best circumstance when the index of refraction of the solvent remains constant (ie. when flow noise is at a minimum) is disproportionally reduced by any change in temperatures of the solvent, which alters its index of refraction and thus increases flow noise.

SUMMARY OF THE INVENTION

Objects of the present invention are: to provide a spectrophotometer detector cell for liquid chromatography that is more accurate and sensitive than previously known types of such detector cells, to provide a detector cell assembly which incorporates an optical system for applying available radiation more efficiently and for more efficient utilization of the exiting light for increasing the sensitivity of measurement, to provide such a detector cell assembly which renders the spectrophotometer substantially insensitive to flow noise due to changes in the refractive index of the solvent, and to provide such a cell in which temperature changes in the sample flowing through the cell are minimized so that the refractive index of the solvent remains substantially constant thereby further enhancing the sensitivity of the absorbance measurement.

In accordance with the invention a spectrophotometer detector cell assembly is formed by a bore through a body of thermally conductive material, such as stainless steel, brass or aluminum whose mass is at least several times larger in volume than of the bore. Inlet and outlet passages for fluid flow are provided through the body wall to the bore, and windows, normally of quartz, are sealed over the ends of the bore. The assembly is mounted for a radiation from a source, such as a deuterium arc to pass through the cell to a photodetector at the other side, the particular wavelength desired being selected by means of a monochromator or filter between the radiation source and the cell.

A tubular inlet conduit from a source of sample material (in a solvent) to be analyzed is made of thermally conductive material, such as stainless steel, brass or aluminum, and connects to the inlet passage of the body for conducting the sample material to the cell bore. A portion of the inlet conduit immediately upstream from the connection to the inlet passage is in thermal contact with the body; in a preferred form the inlet conduit wraps at least once, and preferably three times around the body in thermal contact therewith. Thus, the body and conduit have a heat sink effect on the fluid sample flowing to the cell so that fluid sample material flowing through the cell bore is at a substantially stabilized uniform temperature so that the refractive index of the sample fluid flowing through the cell remains substantially constant, which enhances the sensitivity of the instrument.

A focussing optic, normally a lens, is mounted on the assembly to focus radiation from the source into the cell bore, and is dimensioned and positioned to maximize the amount of focussed radiation within the cell. At the exit end of the cell, a second optical focussing element such as a lens is dimensioned and positioned to concentrate substantially all the radiant energy exiting from the cell onto the photosensitive surface of the photodetector.

DESCRIPTION OF THE DRAWINGS

An illustrative embodiment of the invention is described in detail below with reference to the accompanying drawings in which:

FIG. 1 is an end elevation of a detector cell assembly embodying the present invention;

FIG. 2 is a sectional view taken along the lines 2—2 of FIG. 1, but shown in combination with a source of radiation and photodetector of a spectrophotometer; and FIG. 3 is a schematic representation of the detector cell assembly of FIGS. 1 and 2 illustrating the optical system of the assembly.

DETAILED DESCRIPTION

Referring to FIGS. 1 and 2 of the drawing, a detector cell assembly 10 in accordance with the invention may be made as a separate unit adapted to be inserted as the detector cell in a multi purpose spectrophotometer, or it may be built in. In the embodiment shown the detector cell assembly 10 (indicated with the dash-line box) is shown and described as a composite unit adapted to be inserted in a multi-purpose spectrophotometer instrument. The unit is inserted in position for radiation from a spectrophotometer source 11 of radiation to pass through a windowed end cell 12 of the detector assembly and impinge on the photosensitive surface 13 of a photodetector 14. The photodetector 14 produces output signals proportional to the radiation received, the signals thus being proportional to the amount of light absorbed by a sample fluid flowing through the cell 12. Signals from the photodetector 14 are processed by means well known in the art to provide an analysis in interpretable form, such as a continuous graph produced by a pen recorder.

The source 11 is suitably a deutrium arc lamp and the particular wavelength of the radiation to be applied to the cell 12 is suitably selected by a monochromator or filter (not shown) in the path of the radiation from the source 11 to the cell 12. The windows 16, 17 are made of a suitable radiation transparent material such as quartz and are mounted and sealed over the ends of the cell bore 12 by any suitable means. In the preferred form shown the windows are sealed in place by means of a pressure tight seal of the particular type described in detail in a copending U.S. application Ser. No. 547,380 of Charles F. DeMey. This seal includes thin polytetrafluorethylene gaskets 18, captured respectively between each window 16, 17 and the adjacent surface of the body 15. The windows are each held in place by a bushing 19 having an inward flange 19a bearing against the outer circumferential surface of the window and an outward flange 19b; three or more Bellville washers 20 are placed around each of the bushings 19 and are held under compression against the outward flange 19b by retaining rings 21 which are held in place on the body by screws. The screws 22 (only one of which is shown) are passed through one of the retaining rings 21 and pass through the body 15 to be threaded into the other retaining ring 21, as shown.

The body 15 is made of a thermally conductive material, suitably stainless steel, and has a mass at least several times larger in volume than the cell bore 12. An inlet passage 25 and an outlet passage 26 are drilled through the body 15 to open into enlarged end portions of the cell bore 12, respectively. As indicated in FIGS. 2 and 3, the enlarged end portions of the cell bore 12 are suitably provided by countersinking each end of the bore off-axis to provide a larger bevelled surface at one side through which the inlet and outlet passages 25, 26 open.

At their outer ends, the inlet and outlet passages 25 and 26, are connected respectively to an inlet tube 27 and to an outlet tube 28 which are made of thermally conductive material, such as stainless steel; the connection being suitably made by welding the ends of the tubes 27, 28 into the ends of the inlet and outlet passages 25, 26 respectively. Other materials, such as aluminum or brass might in some cases be used for the body 15 and/or the tubes 27 and 28, but stainless steel is used to enable the instrument to be used for highly corrosive materials.

A portion of the length of the inlet tube 27 immediately upstream from the connection into the inlet passage 25, is in thermal contact with the body 15; in the form shown the inlet tube 27 is wrapped three times around the body 15 before leading off to the connection to a source of the sample material to be analyzed. The latter source is not shown, the connection thereto being indicated by a threaded bushing 29. The outlet tube 28 suitably leads directly to a connection, indicated by threaded bushing 30, to a waste pipe or waste container, not shown.

As shown, a ring 31 is suitably fixed around the outside of the convolutions of the inlet tube 27 around the body 15 to assure good thermal contact of tube convulutions and body.

The relatively large thermal mass of the body 15 in relation to the volume of the cell 12 and to the inlet and outlet passages 25, 26 therethrough, and the thermal contact of a portion of the inlet tube 27 around the body 15, provides a heat sink effect so that by the time the sample fluid being fed in reaches the cell bore 12 its temperature has become substantially equalized with the temperature of the body 15, which due to its thermal mass remains substantially constant during an operative run of the apparatus. In consequence the sample fluid flowing continuously through the cell bore 12 will be at a substantially uniform temperature; the refractive index of the solvent thus remains substantially constant, thereby eliminating flow noise so as to enhance sensitivity and accuracy of the measurements being taken.

The sensitivity of the absorption measurement of a spectrophotometer incorporating a detector assembly 10 of this invention is further enhanced by concentrating more of the available radiation into the cell and by rendering the system substantially insensitive to any flow noise due to any changes in the refractive index of the solvent that may occur. These advantages are provided by an optical system which maximizes the efficient application of available radiation to the fluid in the cell bore, and maximizes the efficient measurement of the amount of radiation exiting from the cell bore. As shown in FIGS. 2 and 3 this optical system includes a lens 35, or other optical focussing system such as a reflective optical system, mounted on the detector assembly 10 (by means not shown) in position to focus radiation from the source 11 into the cell bore 12. In order to get as much of the focussed radiation as possible into the cell bore 12, the lens 35 is dimensioned and positioned so that its focus is as far along in the cell bore 12 as possible without having to lose too much radiation by vignetting at the entrance of the bore cell.

At the exit end of the cell a lens 38, or other optical focussing system such as a reflective optical arrangement, is dimensioned and positioned to collect all the radiation exiting from the cell bore 12, including the widely diverging Schlieren rays and concentrate the radiation on the photodetector 14 by focussing the radiation. The Schlieren rays, indicated by ray traces 39, and other rays, indicated by ray traces 40, will be focussed at different points by the lens 38, but there will be a plane 41 in which the focussing Schlieren rays 39 and other focussing rays 40 intersect and in which the diameter of the area of intersection indicated at 42 will remain constant despite variations or changes in the angular direction of radiation through the cell bore 12. In the preferred embodiment shown, the lens 38 and/or the photodetector 14 are selected and positioned so that the position and diameter of the area 42 coincides with the position and diameter of the area of the photosensitive surface 13 on photodetector 14 in the plane in which the concentrated radiation impinges on the photosensitive surface.

With the foregoing detector cell assembly, the temperature, and hence the refractive index, of the solvent passing through the cell bore 12 is substantially stable. Additionally by maximizing both the effectiveness of the application of the input radiation to fluid in the cell and of the measurement of exiting radiation to the photodetector, the spectrophotometer readings are substantially free of distorting effects of flow noise and are substantially insensitive to changes in the refractive index of the solvent. The detector cell assembly 10 of this invention thus provides a spectrophotometer having greatly improved sensitivity and accuracy.

What is claimed is:

1. A detector cell assembly for use in a spectrophotometer having a source of radiation and a photodetector with a photosensitive surface spaced from the source, said cell assembly being positionable between the radiation source and the photodetector within the spectrophotometer, and comprising:
    a body having an open-ended bore therethrough with radiation transparent windows respectively closing the ends of said bore which thereby defines the spectrophotometer detector cell, said body having an inlet passage and an outlet passage opening into said bore at separate ends thereof for flowing fluid therethrough;
    means for providing a heat sink effect whereby the temperature of the fluid flowing through the cell is maintained substantially constant;
    optical means for focusing the radiation from the source into said bore with the diameter of the radiation being less than the diameter of said bore; and
    energy collecting means interposed between said detector cell and said photosensitive surface for collecting the radiation exiting from said bore and convergently directing it to said photosensitive surface, including the maximum deviated rays of radiation resulting from changes in refractive index of fluid flowing through said cell bore, said energy collecting means and said photosensitive surface being spaced relative to one another such that the maximum deviated rays and principal rays between said energy collecting means and said photosensitive surface intersect in a plane coincident with and defining an area on said photosensitive surface and which area remains substantially constant in size and location on said photosensitive surface for all radiation exiting from the bore;
    said area being located between said energy collecting means and its front focal plane.

2. A detector cell assembly according to claim 1 wherein said body is made of thermally conductive material, and wherein said means for providing a heat sink effect includes an inlet conduit of thermally conductive material having one end thereof connected to said inlet passage and having a portion of its length in direct thermal contact with said body.

3. A detector cell assembly according to claim 1 wherein said energy collecting means includes a lens having a diameter substantially greater than the diameter of said bore.

4. A detector cell assembly for use in a spectrophotometer having a source of radiation and a photodetector with a photosensitive surface spaced from the source, said cell assembly being positionable between the radiation source and the photodetector within the spectrophotometer, and comprising:
    a body having an open-ended bore therethrough with radiation transparent windows respectively closing the ends of said bore which thereby defines the spectrophotometer detector cell, said body being made of thermally conductive material and having an inlet passage and an outlet passage opening into said bore at separate ends thereof for flow of sample therethrough;
    an inlet conduit of thermally conductive material having one end thereof connected to said inlet passage and having a portion of its length in direct thermal contact with said body, heat being exchanged between sample flowing in said inlet conduit and said body to provide a heat sink effect of the body and conduit thereby stabilizing the refractive index of the fluid in the bore and enhancing sensitivity of the photodetector,
    optical means for focusing the radiation from the source into said bore with the diameter of the radiation being substantially the same as the diameter of said bore, and
    energy collecting means interposed between said detector cell and said photosensitive surface for collecting the radiation exiting from said bore and convergently directing it to said photosensitive surface including the maximum deviated rays of radiation due to changes in refractive index of fluid flowing through the cell, said energy collecting means and said photosensitive surface being spaced relative to one another such that the maximum deviated rays and principal rays between said energy collecting means and said photosensitive surface intersect in a plane coincident with and defining an area on said photosensitive surface and which area remains substantially constant in size and location on said photosensitive surface for all radiation exiting from the bore;
    said area being located between said energy collecting means and its front focal plane.

* * * * *

UNITED STATES PATENT AND TRADEMARK OFFICE
CERTIFICATE OF CORRECTION

PATENT NO. : 4,192,614

DATED : March 11, 1980

INVENTOR(S) : Charles F. DeMey, II et al.

It is certified that error appears in the above—identified patent and that said Letters Patent is hereby corrected as shown below:

Column 4, line 62, after "radiation" insert -- on the photodetector 14. --.

Signed and Sealed this

Fifth Day of August 1980

[SEAL]

Attest:

SIDNEY A. DIAMOND

Attesting Officer

Commissioner of Patents and Trademarks